United States Patent [19]
Chiaro et al.

[11] Patent Number: 5,578,762
[45] Date of Patent: Nov. 26, 1996

[54] METHOD AND DEVICE FOR THE VISCOELASTIC PROPERTIES OF POLYMERIC COATINGS OF OPTICAL FIBERS

[75] Inventors: Luisella Chiaro, Caluso; Giorgio Grego, S. Francesco Al Campo; Pada Regio, Castiglione Torinese, all of Italy

[73] Assignee: CSELT - Centro Studi E Laboratori Telecomunicazioni S.p.A., Romoli, Italy

[21] Appl. No.: 418,603

[22] Filed: Apr. 7, 1995

[30] Foreign Application Priority Data

May 5, 1994 [IT] Italy .................................. TO94A0363

[51] Int. Cl.$^6$ ...................................................... G01N 3/02
[52] U.S. Cl. .............................................. 73/860; 73/833
[58] Field of Search ........................... 73/788, 808, 812, 73/813, 831, 833, 849, 853, 856, 860, 150 R, 862.392, 814, 862.4, 789, 790, 795, 800

[56] References Cited

U.S. PATENT DOCUMENTS

| | | | |
|---|---|---|---|
| 1,282,643 | 10/1918 | Scott | 73/860 |
| 3,214,970 | 11/1965 | Flinth | 73/862.392 |
| 3,699,808 | 10/1972 | Ford et al. | 73/772 |
| 3,979,948 | 9/1976 | George et al. | 73/772 |
| 5,297,441 | 3/1984 | Smith et al. | 73/818 |

FOREIGN PATENT DOCUMENTS

| | | |
|---|---|---|
| 0323635 | 7/1989 | European Pat. Off. |
| 2304335 | 3/1991 | Japan . |
| 2104225 | 3/1983 | United Kingdom . |

OTHER PUBLICATIONS

Charles L. Rohn; "Rheological Characterization Of Coatings For Fabrics And Fibers"; Journal of Coated Fabrics, vol. 19–Jan. 1990; pp. 182–192.

Robert J. Overton et al; "Designing And Optical Fiber Dual Coating System For Loose Tube And Ribbon . . . ", Proceedings of 42nd International Wire and Cable Sympsoium–15 Nov. 1993; pp. 701–707.

Buffering Effect Of Fiber Coating And Its Influence On The Proof Test Load In Optical Fibers, Applied Optics, vol. 29, No. 18 20 Jun. 1990, pp. 2682–2685, Ephraim Suhir.

The Seventh European Fibre Optics Communicatiosn and Local Area Networks Exposition, Jun. 27–29, 1990, Munich, Germany, pub. IGI Europe, pp. 77–80.

Interfacial Shearing Stress In Pull–Out Testing Of Dual–Coated Lightguide Specimens, E. Suhir, Journal of Lightwave Technology, vol. 11, No. 12, Feb. 1993.

Journal Of Lightwave Technology, Dec. 1993, USA, Suhir, E., vol. 11, ISSN 0733–8724 Measurements Of Some Physical Characteristics Of The Coating For Optical Fibres Seventh European Fibre Optics Communications, Jun. 27–29, 1990, Munich, Germany.

Applied Optics, vol. 29, No. 18, Buffering Effect Of Fiber Coating And Its Influence On The Proof Test Load In Optical Fibers, Suhir, E. 20 Jun. 1990.

*Primary Examiner*—Richard Chilcot
*Assistant Examiner*—Max Noori
*Attorney, Agent, or Firm*—Herbert Dubno

[57] ABSTRACT

A method and device are provided for measuring the viscoelastic characteristics of polymeric coatings of optical fibers directed on a coated fiber. The ends of the fiber are inserted into a pair of clamps which are shaped in such a way as to hold the coating without tearing it and to allow it to slide longitudinally over the fiber. The clamps impart a relative oscillating motion to the coating creating a longitudinal tensile stress of periodically varying intensity. The clamps and their support are part of a rheometer which measures the opposing stress and processes the stress data to give the desired characteristics.

6 Claims, 1 Drawing Sheet

METHOD AND DEVICE FOR THE VISCOELASTIC PROPERTIES OF POLYMERIC COATINGS OF OPTICAL FIBERS

FIELD OF THE INVENTION

The present invention relates to systems for characterization of fiber materials and, in particular, to a method and device for it concerns a method and device for measuring the viscoelastic properties of polymeric coatings of optical fibers for telecommunications.

BACKGROUND OF THE INVENTION

As is well known, optical fibers are coated during drawing with a polymeric coating intended to protect them from the outside environment. Such a coating comprises, in general, two layers: an inner layer (primary coating), which is relatively soft, and an outer layer (secondary coating) which is more rigid. This structure allows protection of the fiber itself from chemical agents and mechanical actions which could alter its characteristics, e.g. induce attenuation due to microfractures or even cause the fiber to break. However, the coating itself has an influence on the overall behavior of the fiber from the optical and mechanical point of view. This influence depends not only on the type of coating material, but also on the coating application and polymerization processes. To fully characterize the fiber, it is therefore important to know the characteristics of the coating, and in particular the viscoelastic characteristics (viscous modulus, elastic modulus, glass transition temperature . . . ).

The techniques proposed until now to determine these characteristics are based on the analysis of the behavior of isolated, film-shaped polymer samples. The characterization of optical fiber coatings using these techniques is described, for instance, in the papers "Designing an optical fiber dual coating system for loose tube and ribbon cable long line and local loop applications", by R. J. Overton et al., Proceedings of 42nd International Wire and Cable Symposium, pages 701–707, and "Rheological Characterization of Coatings for Fabrics and Fibers", by C. L. Rohn, Clemson University Conference on Coated Fabrics, 2–3 May 1989, Clemson (USA), paper number 671.

In these methods, the sample undergoes a periodically variable deformation, applied by means of a suitable instrument (rheometer) and the resistant torque or stress is measured. From the measured quantity, the elastic modulus, the viscous modulus, the glass transition temperature, etc., of the sample are calculated; by extrapolating the data thus found, the behavior with time of the coated fiber is determined.

It is clear that, due to the different geometric characteristics, the response of a film to a mechanical deformation is very different from that of a cylinder, in particular because of the existence in the former case of boundary effects. Moreover, this type of measurement does not take into account the influence of the fiber on the coating due to adhesion forces. Simple extrapolation of the measurements on the isolated sample is not sufficient to provide reliable data on the behavior of a coating in operating conditions.

OBJECT OF THE INVENTION

It is an object of the present invention to provide a method and device for the measurement of the viscoelastic characteristics of polymeric coatings of optical fibers, which allow the measurement to be performed on the final product, i.e. on the coated fiber, and thus in operating conditions.

SUMMARY OF THE INVENTION

According to the invention, a method is provided wherein the sample is subjected to a periodically variable deformation, the resistant stress is measured, and the desired characteristics are obtained from the measured stress values, and wherein, furthermore:

the ends of a fiber span equipped with the coating are inserted into a pair of holding elements, capable of holding the coating without tearing it while allowing sliding thereof over the fiber;

a tensile pre-stress is applied to the coating; and a relative oscillating motion is imparted to the holding elements, thereby inducing an essentially longitudinal tensile deformation whose intensity periodically varies about the value of the pre-stress applied to the coating.

The device according to the invention is pan of an apparatus comprising means for imparting a periodic tensile deformation to a sample under test, means for measuring the opposing stress of the sample and data processing means to determine the viscoelastic characteristics starting from the measured stress, and it forms the means to apply the periodic deformation. Such device further comprises a pair of elements capable of holding the ends of the coating applied on a fiber, without tearing it and allowing it to slide over the fiber, and to apply a tensile pre-stress to the coating, and means to impart an oscillating motion to at least one of said elements.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
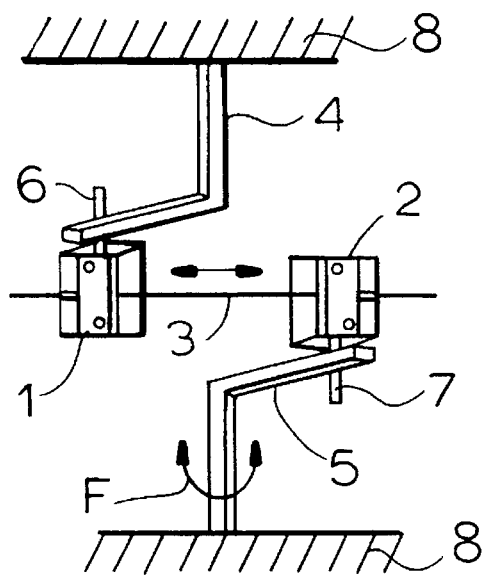
FIG. 1 is a diagrammatic side elevational view of a device for measuring viscoelastic properties of the coating.

The device which performs the method according to the invention is incorporated into a rheometer, i.e. an apparatus that obtains the viscoelastic characteristics of a material starting from the values of the opposing stress exerted by a sample of material undergoing a periodic deformation. For example, the apparatus to which this invention has been applied is the RDA-2 by Rheometrics, Inc., of Piscataway (N.J., USA). A complete description of the apparatus is not necessary to understand the invention.

The device comprises essentially a pair of clamps 1, 2 in which there are held the ends of a fiber span 3 equipped with a coating whose viscoelastic characteristics need to be determined and means for imparting, an oscillatory motion to one of the clamps 1, 2 to subject fiber 3 to a longitudinal oscillatory deformation. The means for imparting the oscillatory motion to the clamp depend on the type of rheometer and/or on the type of accessories it is equipped with. For example, the aforesaid apparatus is provided with a pair of arms 4, 5 one of which (e.g. arm 4) is fixed while the other one is rotatable around a vertical axis, in either direction, as indicated by arrow F. In an exemplary embodiment of the invention, the rotation angles imparted to arm 4 were of the order of a fraction of a degree. Clamps 1, 2 are pivotally mounted by means of pivots 6, 7 at the ends of said arms. By this arrangement, the angular displacements of arm 5 are transformed into linear displacements of clamp 2. Reference 8 represents the fixed part of the rheometer carrying arms 4, 5.

Figure 2:
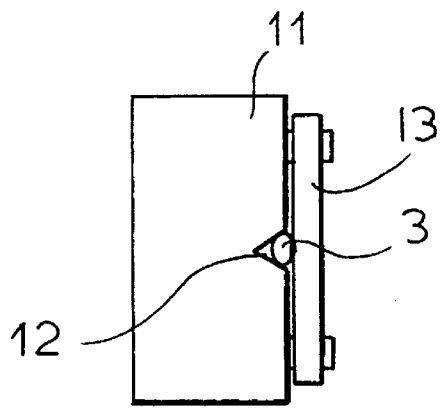
FIG. 2 is a section of a clamp.
Figure 3:
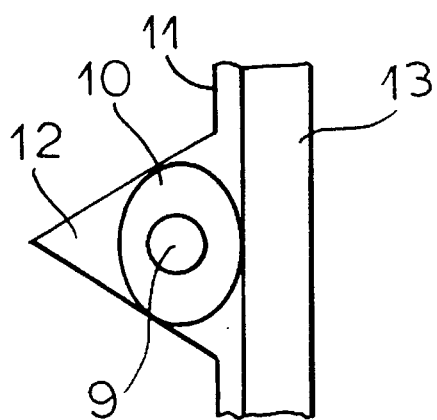
FIG. 3 is an enlarged view of the groove of the clamp and of the fiber.

As can be seen in FIG. 3, from the mechanical point of view fiber 3 can be seen as the set of an essentially rigid central part 9 (comprising the core and the cladding made of silica or other material used for optical fibers, and hereinafter called for the sake of simplicity "the silica") and by an outer part 10 which is partially elastic ("the coating"), though in reality, as mentioned above, coating 10 comprises in general two layers having different characteristics. Fiber span 3 between the two clamps may have a length of a few centimeters, e.g. about 2 cm. Clamps 1, 2 must be such as to hold coating 10 without tearing it, allowing it at the same time to slide longitudinally over silica 9. For example, as can be seen in FIGS. 2 and 3, a clamp may include a body 11 with a V-shaped groove 12 into which coated fiber 3 is introduced and a holding plate 13 which retains coated fiber 3 in groove 12. By this arrangement, by suitably choosing the dimensions of the groove, it is possible to apply to fiber 3 a compression stress which is distributed on three points of the outer circumference of the fiber and which causes a deformation only in coating 10.

To carry out the measurements, fiber 3 is fixed between clamps 1, 2, and arm 5 is rotated by such an angle as to subject the fiber itself to a pre-stress, e.g. of the order of 1N. Subsequently, arm 5 is made to oscillate to impart to clamp 2 an oscillatory motion of suitable frequency (e.g. a few Hertz) and of such an amplitude as to always maintain the fiber under tension, to cause, in the fiber, a nearly longitudinal oscillatory deformation which, given the forces involved, in practice interests only the coating. For instance, the amplitude of the oscillation of the force applied to the fiber to obtain the deformation may be a few tenths of a Newton. The instrument measures the opposing stress and the data processing programs contained in it (Rhios software) derive from the opposing stress the values of the quantities of interest, for example elastic modulus G', viscous modulus G", the phase difference between deformation and measured stress, of which the tangent corresponds to ratio G"/G'. The relationships linking such quantities to the measured stress are well known and are reported for example in the above mentioned paper by C. L. Rohn.

As previously stated, the deformation has to occur in a linear viscoelastic region of the coating material, since only in this region can the correlation between the measured stress and the various quantities be established. Therefore, before subjecting the fiber to the oscillatory deformation, it is necessary to identify such area: this can easily be accomplished by carrying out measurements with different deformations and at different temperatures.

Depending on the measurements to carry out, the frequency and/or the amplitude of the oscillations can be varied and, for a given deformation applied, a temperature scanning can be performed to determine the glass transition temperature.

Figure 4:
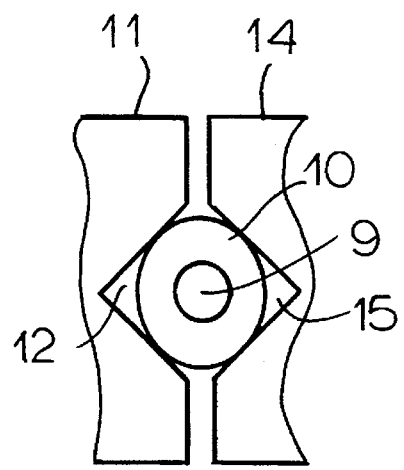
FIG. 4 is an enlarged view of another embodiment of the clamp in FIG. 2.

It is evident that what is described herein is given solely by way of non-limiting example and that variations and modifications are possible without departing from the scope of the invention. For example, as can be seen in FIG. 4, holding plate 13 may be replaced by a second block 14 identical to the first and provided with its own groove 15, opposite to groove 12. In this case, grooves 12, 15 will be shaped so that their walls apply the compression to coating 10. Further, clamps 1, 2 may be realized by means of jaw-type devices, or they may be fixed on supports moving with relative oscillatory motion.

We claim:

1. A method of measuring viscoelastic characteristics of a polymeric coating of a coated optical fiber, comprising the steps of:
   (a) engaging the polymeric coating of a sample of the coated optical fiber at spaced-apart locations with respective clamps so compressing outer surfaces of the coating as not to tear the coating but to permit relative movement between said outer surface of said coating and the optical fiber;
   (b) applying a tensile prestress to said coating;
   (c) while said coating is under said tensile prestress imparting relative oscillating motion to said clamps to subject said coating to a longitudinal prestress of an intensity varying about a value of said prestress, thereby subjecting said coating to periodically variable deformation; and
   (d) measuring opposing stress during step (c) and determining said viscoelastic characteristics of said coating from the measured opposing stress.

2. The method defined in claim 1 wherein said variation of intensity is effected at an interval such as to maintain the coating under a tensile stress and within a linear viscoelastic region of material of the coating.

3. A device for measuring viscoelastic characteristics of a polymeric coating of a coated optical fiber, said device comprising:
   a pair of clamps engaging the polymeric coating of a sample of the coated optical fiber at spaced apart locations so as to compress outer surfaces of the coating without tearing the coating and permitting relative movement between the outer surface of said coating and the optical fiber;
   respective supports for said clamps for applying a tensile prestress to said coating; and
   means for imparting an oscillatory movement to at least one of said supports for imparting relative oscillating means to said clamps while said coating is under prestress to subject said coating to a longitudinal tensile stress of an intensity varying about a value of prestress, thereby subjecting said coating to periodically variable deformation, said supports and said clamps being part of an apparatus measuring opposing stress during oscillation of said one of said supports and determining said viscoelastic characteristics of said coating from the opposing stress.

4. The device defined in claim 3 wherein each of said clamps has a V-shaped groove receiving the optical fiber and engaging the coating thereof and a second body pressing said fiber into said groove, the groove being dimensioned so that application of said second body onto said first body causes compression of said coating at at least three points.

5. The device defined in claim 4 wherein said second body is a plate.

6. The device defined in claim 4 wherein said second body has an element formed with another V-shaped groove engaging said coating at two locations.

* * * * *